(12) United States Patent
Kasahara

(10) Patent No.: US 11,744,545 B2
(45) Date of Patent: Sep. 5, 2023

(54) ULTRASONIC DIAGNOSIS SYSTEM CONFIGURED TO GENERATE PROBE OPERATION SUPPORT INFORMATION, AND OPERATION SUPPORT METHOD

(71) Applicant: FUJIFILM Healthcare Corporation, Chiba (JP)

(72) Inventor: Eiji Kasahara, Chiba (JP)

(73) Assignee: FUJIFILM Healthcare Corporation, Chiba (JP)

( * ) Notice: Subject to any disclaimer, the term of this patent is extended or adjusted under 35 U.S.C. 154(b) by 21 days.

(21) Appl. No.: 17/457,065

(22) Filed: Dec. 1, 2021

(65) Prior Publication Data

US 2022/0175345 A1 Jun. 9, 2022

(30) Foreign Application Priority Data

Dec. 8, 2020 (JP) ................................. 2020-203297

(51) Int. Cl.
*A61B 8/14* (2006.01)
*A61B 8/08* (2006.01)
*A61B 8/00* (2006.01)

(52) U.S. Cl.
CPC .............. *A61B 8/14* (2013.01); *A61B 8/0883* (2013.01); *A61B 8/4254* (2013.01); *A61B 8/463* (2013.01); *A61B 8/5207* (2013.01)

(58) Field of Classification Search
CPC ....... A61B 8/0883; A61B 8/4245; A61B 8/54; A61B 8/4254; G06T 7/70
See application file for complete search history.

(56) References Cited

U.S. PATENT DOCUMENTS

| 2005/0148852 A1* | 7/2005 | Tank | A61B 8/00 600/407 |
| 2005/0154305 A1* | 7/2005 | Kamiyama | G01S 7/52085 600/443 |
| 2008/0187193 A1* | 8/2008 | Hoctor | G06V 30/142 382/128 |

(Continued)

FOREIGN PATENT DOCUMENTS

| EP | 27696767 A1 | 8/2014 |
| JP | 2004-016268 | 1/2004 |
| JP | 2013-255658 | 12/2013 |

OTHER PUBLICATIONS

European Search Report dated May 3, 2022 in connection with corresponding European Patent Application No. 21212442.4.

*Primary Examiner* — Joel Lamprecht
*Assistant Examiner* — Nyrobi Celestine
(74) *Attorney, Agent, or Firm* — Paul Teng

(57) ABSTRACT

A current cross section searching unit identifies a current cross section corresponding to a scan plane by setting a group of provisional cross sections with respect to a tissue model corresponding to a target tissue, and calculating a degree of similarity between data of each provisional cross section and tomographic image data. An operation support information generating unit generates operation support information from difference information indicating a spatial relationship between the current cross section and a target cross section (corresponding to an observation cross section). The group of provisional cross sections set with respect to the tissue model is narrowed down based on a camera image.

9 Claims, 12 Drawing Sheets

(56) References Cited

U.S. PATENT DOCUMENTS

| | | | |
|---|---|---|---|
| 2013/0144135 A1* | 6/2013 | Mahfouz | A61B 34/10 600/309 |
| 2014/0219524 A1* | 8/2014 | Takeguchi | G16H 50/30 382/128 |
| 2014/0235998 A1 | 8/2014 | Kim et al. | |
| 2015/0173705 A1* | 6/2015 | Lee | A61B 5/055 600/407 |
| 2016/0157831 A1* | 6/2016 | Kang | G06T 7/0012 600/443 |
| 2016/0270757 A1 | 9/2016 | Isahaya et al. | |
| 2017/0071492 A1* | 3/2017 | van Dam | A61B 5/282 |
| 2017/0337731 A1* | 11/2017 | Jago | A61B 8/54 |
| 2018/0008232 A1* | 1/2018 | Mine | A61B 8/466 |
| 2018/0308238 A1* | 10/2018 | Park | A61B 8/469 |
| 2019/0357987 A1* | 11/2019 | Harks | A61B 34/20 |
| 2020/0196979 A1* | 6/2020 | Van Heesch | A61B 8/4254 |
| 2020/0273184 A1 | 8/2020 | Dufour et al. | |

\* cited by examiner

FIG. 2

| TARGET TISSUE (48) | EXAMINEE BODY POSITION (50) | TYPE OF APPROACH (52) | TISSUE MODEL (54) | OBSERVATION CROSS SECTION (56) | TARGET CROSS SECTION POSITION (58) |
|---|---|---|---|---|---|
| HEART | SUPINE | A | HEART MODEL 1 | LONG-AXIS VIEW | ... |
| | | | | SHORT-AXIS VIEW | ... |
| | | | | ... | ... |
| | | B | HEART MODEL 2 | 4-CHAMBER VIEW | ... |
| | | | | 2-CHAMBER VIEW | ... |
| | | | | ... | ... |
| | LATERAL RECUMBENT | C | HEART MODEL 3 | LONG-AXIS VIEW | ... |
| | | | | SHORT-AXIS VIEW | ... |
| | ... | ... | ... | ... | ... |
| ... | ... | ... | ... | ... | ... |

46, 28A, 40A

ULTRASONIC DIAGNOSIS SYSTEM CONFIGURED TO GENERATE PROBE OPERATION SUPPORT INFORMATION, AND OPERATION SUPPORT METHOD

CROSS REFERENCE TO RELATED APPLICATION

This application claims priority to Japanese Patent Application No. 2020-203297 filed on Dec. 8, 2020, which is incorporated herein by reference in its entirety including the specification, claims, drawings, and abstract.

TECHNICAL FIELD

The present disclosure relates to an ultrasonic diagnosis system and an operation support method, and more particularly to a technology for supporting probe operation.

BACKGROUND

An ultrasonic diagnosis system is a system that performs transmission and reception of ultrasound with respect to an examinee and forms an ultrasound image based on signals obtained thereby. An ultrasonic diagnosis system is composed of an ultrasonic diagnosis apparatus, or an ultrasonic diagnosis apparatus with various devices connected thereto.

At the time of ultrasonic examination, a probe (i.e., an ultrasound probe) is abutted against a surface of an examinee's body (i.e., a living body), and while in that state, ultrasound waves are transmitted from the probe to the interior of the examinee's body, and reflected waves from the interior of the living body are received by the probe. The probe (more precisely, the probe head) is an ultrasound transmitter-receiver that is held by an examiner (e.g., a medical doctor or a medical technologist). By means of the probe, a scan plane (i.e., a beam scan plane) that serves as a two-dimensional data capturing region is created.

It is not easy to precisely align a scan plane with an observation cross section (i.e., a cross section that should be diagnosed) in a target tissue. In other words, proficiency is required for performing accurate and speedy probe operation. It is also not easy to precisely align a current scan plane with a past observation cross section. In light of this, some technologies for supporting probe operation have been suggested. For example, Document 1 (JP 2004-16268 A) discloses an ultrasonic diagnosis apparatus having a function to display navigation information for supporting probe operation.

Document 2 (JP 2013-255658 A) discloses an ultrasonic diagnosis apparatus comprising a camera. In this ultrasonic diagnosis apparatus, a body surface position and a probe position are identified based on a camera image. Neither Document 1 nor Document 2 describes using a tissue model for probe navigation.

The present disclosure is directed to providing, to an examiner, probe operation support information for causing a scan plane to coincide with an observation cross section. Alternatively, the present disclosure is directed to generating the probe operation support information by a simple configuration.

SUMMARY

An ultrasonic diagnosis system according to the present disclosure includes: a former configured to form a tomographic image based on information obtained from a scan plane created by a probe; a searcher configured to identify a current model cross section corresponding to the scan plane by comparing the tomographic image to a group of provisional model cross sections set with respect to a tissue model reflecting a three-dimensional structure of a target tissue; and a generator configured to generate, based on the current model cross section, probe operation support information for causing the scan plane to approach an observation cross section in the target tissue.

An operation support method according to the present disclosure includes: a step of comparing a tomographic image, which is formed based on information obtained from a scan plane created by a probe, to a group of provisional model cross sections set with respect to a tissue model reflecting a three-dimensional structure of a target tissue, thereby identifying a current model cross section corresponding to the scan plane; and a step of generating probe operation support information based on a spatial relationship between the current model cross section and a target model cross section in the tissue model.

BRIEF DESCRIPTION OF DRAWINGS

Embodiment(s) of the present disclosure will be described based on the following figures, wherein:

FIG. 2 is a diagram for explaining management of tissue models and observation cross sections;

DESCRIPTION OF EMBODIMENTS

Figure 1:
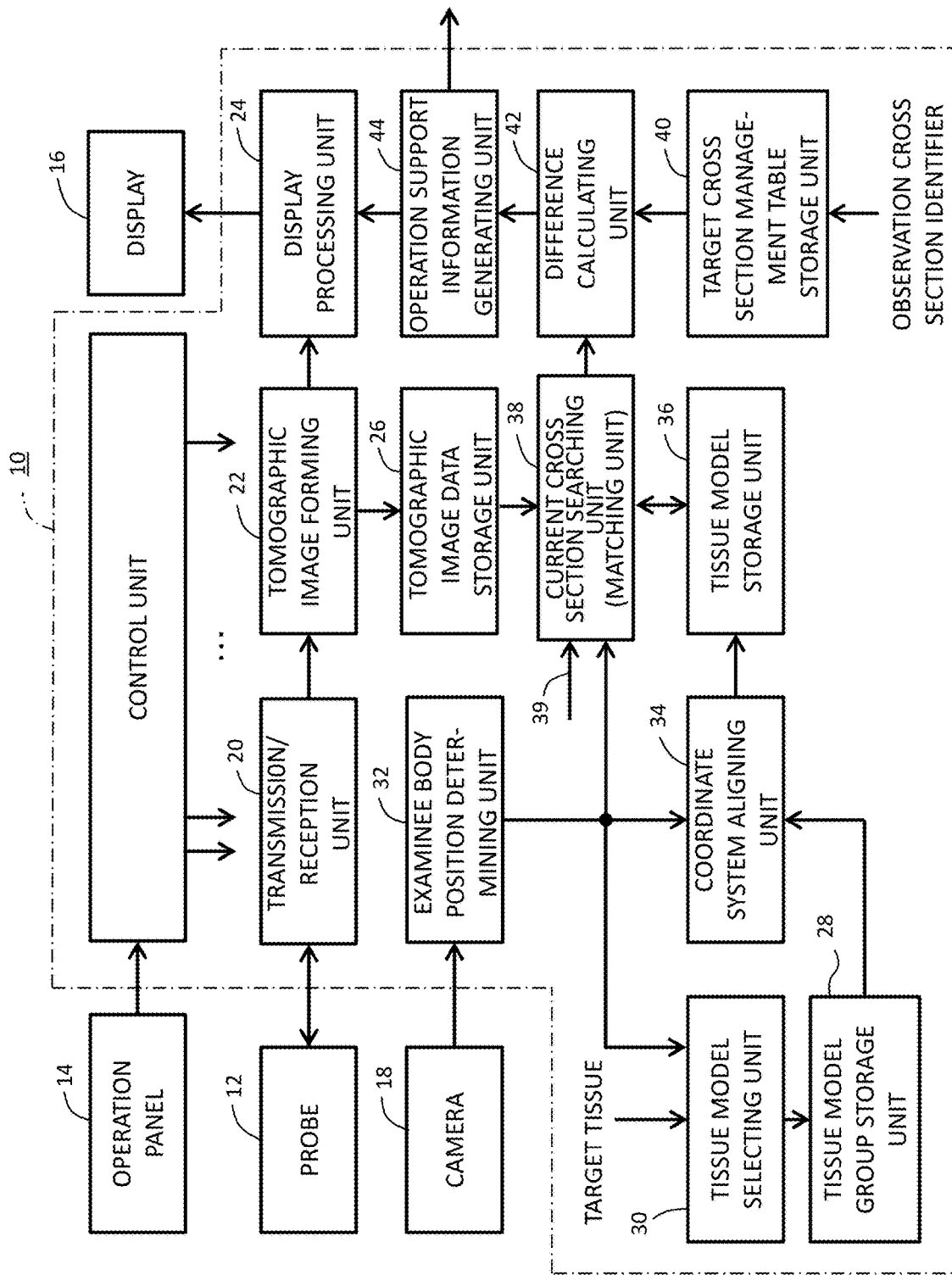
FIG. 1 is a block diagram illustrating an ultrasonic diagnosis system according to an embodiment.

Embodiments will now be described by reference to the drawings.

(1) Overview of Embodiments

An ultrasonic diagnosis system according to an embodiment comprises a tomographic image forming unit, a search unit, and a support information generating unit. The tomographic image forming unit forms a tomographic image based on information obtained from a scan plane created by a probe. The search unit identifies a current model cross section corresponding to the scan plane by comparing the tomographic image to a group of provisional model cross sections set with respect to a tissue model reflecting a three-dimensional structure of a target tissue. The support information generating unit generates, based on the current model cross section, probe operation support information for causing the scan plane to approach an observation cross section in the target tissue. The tomographic image forming unit can be referred to as a former. The search unit can be referred to as a searcher. A support information generating unit can be referred to as a generator.

According to the above-described configuration, the position of the current model cross section; i.e., the current scan plane, can be easily identified using the tissue model. By moving the probe according to the probe operation support information, the scan plane can be caused to approach the observation cross section in the target tissue. In this way, it is possible to support probe operation by an examiner.

A degree of similarity between each of the provisional model cross sections and the tomographic image may be calculated, and from among the group of provisional model cross sections, the provisional model cross section having the highest similarity to the tomographic image may be identified as the current model cross section (i.e., the cross section corresponding to the scan plane). When the spatial relationship of the probe and/or the target tissue with respect to the tissue model is unknown, an extremely large number of provisional model cross sections must be set with respect to the target tissue. In such a case, the amount of calculation for searching the current model cross section is increased disadvantageously. Accordingly, the spatial relationship of the probe and/or the target tissue with respect to the tissue model may be determined, and the group of provisional model cross sections set with respect to the target tissue may be narrowed down based on this spatial relationship. In that case, the spatial relationship may be determined based on a camera image.

An ultrasonic diagnosis system according to an embodiment includes a model storage unit having a plurality of tissue models stored therein. The model storage unit is composed of a memory. From among the plurality of tissue models, a specific tissue model corresponding to the target tissue is selected. With respect to the specific tissue model, a group of provisional model cross sections is set. A tissue model may be provided for each tissue, or alternatively, for each examined portion of a tissue. For example, a tissue model is a set of volume data obtained by ultrasound transmission and reception. Artificial three-dimensional data, 3D data obtained by other medical apparatuses such as a CT, and the like may also be used as a tissue model. In any case, each tissue model is a set of data reflecting a three-dimensional structure (or three-dimensional form) of a target tissue, and is a set of data provided in advance. Data obtained from an examinee different from the examinee to be currently examined may be used as a tissue model.

In an ultrasonic diagnosis system according to an embodiment, a target model cross section corresponding to the observation cross section is determined in a tissue model, and the support information generating unit generates the probe operation support information based on a spatial relationship between the current model cross section and the target model cross section in the tissue model. In an embodiment, a difference between the position of the current model cross section and the position of the target model cross section in the tissue model coordinate system is calculated as difference information, and the probe operation support information is generated based on this difference information. The observation cross section is a cross section that should be examined or diagnosed in the target tissue, and an examination protocol generally defines a plurality of observation cross sections. A cross section regarding which observation was performed in the past may be registered as the observation cross section. According to the above-described configuration, the difference information can be generated based on the simulated spatial relationship between the current model cross section and the target model cross section in the tissue model coordinate system, which replaces the real spatial relationship between the scan plane and the observation cross section. Although a positioning system (e.g., a positioning system using a three-dimensional magnetic field generator and a magnetic sensor) for detecting the position and orientation of the probe may be provided, according to the above-described configuration, the difference information can be generated in a simple manner without employing a complex configuration comprising a positioning system or the like.

An ultrasonic diagnosis system according to an embodiment includes: a camera that captures the examinee against whom the probe is abutted, thereby obtaining a camera image; and an examinee body position determining unit that determines the examinee's body position based on the camera image. The examinee body position determining unit can be referred to as a first determiner. Based on the examinee's body position, the search unit sets a group of provisional model cross sections with respect to a tissue model. According to this configuration, the group of provisional model cross sections set with respect to the tissue model can be narrowed down based on the examinee's body position. The tissue model coordinate system and the examinee coordinate system may be correlated based on the examinee's body position. For example, when the examinee is in a lateral recumbent position, the tissue model may be turned sideways in accordance with that body position. While the coordinate system may be actually rotated, the coordinate system may alternatively be rotated logically. The range of area in which the group of provisional model cross sections is set is changed in accordance with the examinee's body position.

An ultrasonic diagnosis system according to an embodiment includes: a camera that captures the examinee against whom the probe is abutted thereby obtaining a camera image; and a probe position determining unit that determines the position of the probe based on the camera image. The probe position determining unit can be referred to as a second determiner. Based on the probe position, the search unit sets a group of provisional model cross sections with respect to a tissue model. According to this configuration, the group of provisional model cross sections set with respect to the target tissue can be narrowed down based on the probe position.

An ultrasonic diagnosis system according to an embodiment includes: a camera that captures the examinee against whom the probe is abutted, thereby obtaining a camera image; and a model selecting unit that selects, from among a plurality of tissue models, a specific tissue model corresponding to the target tissue based on the camera image. The model selecting unit can be referred to as a selector. According to this configuration, a tissue model corresponding to the target tissue to be diagnosed can be automatically selected from among a plurality of tissue models, so that burden on the user can be reduced. The target tissue may be identified from the examinee's body position and the probe position, and a specific tissue model corresponding to the target tissue may be selected accordingly.

In an embodiment, the support information generating unit generates, as the probe operation support information, a plurality of sets of operation instruction information in a stepwise manner. Examples of types of probe operation include translational movement in the forward/rearward direction, translational movement in the rightward/leftward direction, rotational movement about the central axis of the probe, rotational movement about an axis along the electronic scan direction, and the like. When a plurality of sets of operation instruction information are simultaneously provided, the operator is likely to be confused. However, when the sets of operation instruction information are provided stepwise, the operator is unlikely to be confused.

An operation support method according to an embodiment includes: a step of comparing a tomographic image, which is formed based on information obtained from a scan plane created by a probe, to a group of provisional model cross sections set with respect to a tissue model reflecting a three-dimensional structure of a target tissue, thereby identifying a current model cross section corresponding to the scan plane; and a step of generating probe operation support information based on the spatial relationship between the current model cross section and a target model cross section in the tissue model.

The above-described operation support method can be implemented as a software function. In that case, a program for carrying out the above-described operation support method is installed via a portable storage medium or a network into an ultrasonic diagnosis system that serves as an information processing device. The information processing device has a non-transitory storage medium that stores the above-noted program. The concept of the information processing device includes that of a computer, an ultrasonic diagnosis apparatus, an ultrasonic diagnosis system, and the like.

(2) Details of Embodiments

In FIG. 1, an ultrasonic diagnosis system according to an embodiment is shown as a block diagram. The ultrasonic diagnosis system is a medical system to be provided in a medical institution such as a hospital. By means of the ultrasonic diagnosis system, transmission and reception of ultrasound is performed with respect to an examinee, and based on information obtained thereby, an ultrasound image representing a tissue inside the examinee is formed. A tissue that serves as a target of diagnosis is, for example, the heart, the liver, a kidney, a fetus, a mammary gland, or the like.

The ultrasonic diagnosis system has a main unit (i.e., an ultrasonic diagnosis apparatus main unit) 10. The main unit 10 is composed of electronic circuits, processors, storage units, and so on. Each processor is, for example, a CPU that executes programs. In FIG. 1, a plurality of functions exhibited by the processors are represented by a plurality of blocks (see reference numerals 24, 30, 32, 34, 38, 42, and 44). A probe (i.e., an ultrasound probe) 12, an operation panel 14, a display 16, a camera 18, and the like are connected to the main unit 10.

The operation panel 14 is an input device comprising switches, buttons, a trackball, a keyboard, and the like. The display 16 is composed of an LCD, an organic EL display device, or the like. The camera 18 is a device that captures an examinee against whom the probe is abutted, and is composed of a black-and-white camera or a color camera.

The probe 12 is composed of a probe head, a cable, and a connector. Inside the probe head, there is provided a transducer element array comprising a plurality of transducer elements disposed in a linear or arc-shaped arrangement. Ultrasound waves are transmitted from the transducer element array to the interior of the examinee's body, and reflected waves from the interior of the living body are received by the transducer element array. More specifically, an ultrasound beam (i.e., transmission and reception beams) is formed by the transducer element array, and by electronically scanning the beam, a scan plane (i.e., a beam scan plane) is created. As electronic scan methods, an electronic sector scan method, an electronic linear scan method, and the like are known. An ultrasound transmission/reception surface of the probe head is abutted against a surface of the examinee's body while the probe head is held by an examiner, who is the user. The probe head is the main part of the probe, and the probe head is hereinafter simply referred to as the probe 12. The connector is detachably connected to the main unit 10. Instead of a one-dimensional transducer element array, a two-dimensional transducer element array may alternatively be provided.

A transmission/reception unit 20 is an electronic circuit that functions as a transmission beamformer and a reception beamformer. At the time of transmission, a plurality of transmission signals are supplied in parallel from the transmission/reception unit 20 to the transducer element array, thereby forming a transmission beam. At the time of reception, when reflected waves from the interior of the living body are received at the transducer element array, a plurality of reception signals are output from the transducer element array to the transmission/reception unit 20. In the transmission/reception unit 20, reception beam data are generated by performing phase alignment and summing (i.e., delay and summing) of the reception signals. Typically, one set of reception frame data is constructed by one scan of the ultrasound beam. One set of reception frame data is constituted of a plurality of sets of reception data located serially along the electronic scan direction. One set of reception data is constituted of a plurality of sets of echo data located serially along the depth direction. The electronic scan of the ultrasound beam is repeated, and a plurality of sets of reception frame data are thereby generated in a repeated manner. Such sets of reception frame data constitute a reception frame data array.

A tomographic image forming unit 22 is a former that generates a tomographic image data array based on a reception frame data array. Specifically, the tomographic image forming unit 22 includes a digital scan converter (DSC). The DSC is an exclusive processor having functions such as a coordinate conversion function, a pixel interpolation function, and a frame rate conversion function. Each tomographic image data array is transmitted to a display processing unit 24 and a tomographic image data storage unit 26. The tomographic image data storage unit 26 temporarily stores individual sets of tomographic image data for the purpose of a matching processing described further below. The individual tomographic images are B-mode tomographic images.

The display processing unit 24 has an image synthesis function, a color calculation function, and the like. In the display processing unit 24, images to be displayed on the display 16 are generated. The images to be displayed include tomographic images in the form of a moving image. In an embodiment, operation support information for supporting probe operation, or for probe navigation, is displayed on the display 16.

The camera 18 is a device that obtains a camera image for determining the examinee's body position or the like. The camera 18 is installed at a position capable of obtaining such a camera image. For example, when the examiner is located on one side of a bed on which the examinee is placed, the camera 18 is installed at a position above the other side of the bed and is directed diagonally downward. The camera 18 may be installed on the ceiling and directed downward. Installation of a plurality of cameras may be contemplated.

An examinee body position determining unit 32 is a first determiner that determines the examinee's body position based on a camera image. For example, a body position type such as a supine position, a lateral recumbent position, or the like is determined. As the examinee body position determining unit 32, a machine-learned determiner or estimator may be used.

A tissue model group storage unit 28 has stored therein a plurality of tissue models corresponding to a plurality of tissues. For one tissue (e.g., the heart), one tissue model may be provided, or a plurality of tissue models may be provided. A tissue model may be provided for each examinee body position. Each of the individual tissue models may be a set of ultrasound volume data obtained by ultrasound transmission and reception, or may alternatively be a set of 3D data obtained by a CT device or MRI device, or a set of artificially-generated 3D data. Each tissue model is three-dimensional data in a three-dimensional memory space, and is data that reflects a three-dimensional structure of a tissue (i.e., represents or simulates a three-dimensional structure of a tissue).

A tissue model selecting unit 30 is a selector that selects, in accordance with a target tissue, a specific tissue model from among a plurality of tissue models stored in the tissue model group storage unit 28. The target tissue is designated by the user, or is determined from electronic medical record information or the like. As described further below, the target tissue may be determined based on a camera image. For example, the target tissue may be determined based on the examinee's body position and the probe position, and a specific tissue model may be selected based thereon.

In the example configuration shown, data representing the selected specific tissue model are transmitted to a coordinate system aligning unit 34. The coordinate system aligning unit 34 is a means for aligning the examinee coordinate system and the tissue model coordinate system. In aligning the coordinate systems, the data representing the tissue model may be subjected to an operation such as rotation, or the two coordinate systems may be linked logically.

The data representing the tissue model after the coordinate system alignment are stored in a tissue model storage unit 36. From this stored data representing the tissue model, a plurality of sets of provisional cross section data (i.e., a plurality of sets of provisional model cross section data) are sequentially read out. Here, it is possible to sequentially read out the plurality of sets of provisional cross section data from the tissue model group storage unit 28, without separately providing the tissue model storage unit 36.

A current cross section searching unit 38 is a searcher that successively compares a tomographic image to a group of provisional cross sections set with respect to the tissue model stored in the tissue model storage unit 36, thereby determining a degree of similarity of each provisional cross section. The provisional cross section that resulted in the best similarity is identified as the current cross section (i.e., the current model cross section) corresponding to the scan plane. More specifically, between each of the sets of provisional cross section data and the tomographic image data, a correlation calculation is performed, and a degree of similarity, which is a correlation value, is thereby computed. Based on the computed plurality of values of degree of similarity, the current cross section is determined. The series of processing for calculating the correlation values can be referred to as a pattern matching processing. Parameters of the group of provisional cross sections such as the pitch, number of cross sections, and the like are designated in advance by the user, or are designated automatically according to set conditions.

Although it is theoretically possible to set a large number of provisional cross sections with respect to a tissue model, in an embodiment, the group of provisional cross sections to be actually set is narrowed down based on information such as the examinee's body position, the probe position, and the like. In other words, only a certain limited group of provisional cross sections having a likelihood of matching is set. As a result, the required amount of calculation can be reduced, and matching accuracy can be enhanced. The provisional cross section that results in the best similarity is recognized as the current cross section corresponding to the scan plane in the three-dimensional space inside the living body. The position of the current cross section in the tissue model corresponds to the position of the scan plane in the actual three-dimensional space. As shown by reference numeral 39, information such as the probe position and the type of approach, in addition to information indicating the examinee's body position, may be supplied to the current cross section searching unit 38. Based on such information, the group of provisional cross sections to be set with respect to the tissue model is narrowed down.

A target cross section management table storage unit 40 has stored therein information that identifies a plurality of target cross sections. The plurality of target cross sections are cross sections to be set with respect to tissue models, and correspond to actual observation cross sections. For example, positions of individual target cross sections in each tissue model are managed. In that case, three points included in each target cross section may be managed, or a representative coordinate information of each target cross section may be managed. During progress along an examination protocol, a plurality of observation cross sections are designated, and a plurality of target cross sections are selected accordingly. At the time of performing a difference calculation, an identifier that identifies an observation cross section is supplied to the target cross section management table storage unit 40.

A difference calculating unit 42 is a calculator that calculates difference information based on spatial relationship between the current cross section and a target cross section in a tissue model. Specifically, a difference between the position of the current cross section and the position of the target cross section is calculated as the difference information. For example, based on the tissue model coordinate system, six-dimensional coordinate values ($\Delta x$, $\Delta y$, $\Delta z$, $\Delta \theta x$, $\Delta \theta y$, $\Delta \theta z$) are determined as the difference information. The difference information in the tissue model coordinate system may subsequently be converted into difference information in the examinee coordinate system. In any case, coordinate information necessary for generating operation support information is generated. Difference information according to a probe-based coordinate system may be calculated.

An operation support information generating unit 44 is a generator that generates operation support information based on the difference information. For example, the operation support information is operation guide images, operation guide voice, and the like. The type of information to be generated may be selected by the user. In the display processing unit 24, operation guide images are integrated into display images. The operation guide images are displayed on the screen of the display 16. Operation guide voice may be output from a speaker (not shown in the drawings).

When a plurality of operation instructions are simultaneously provided, the operator is likely to become confused. Accordingly, it is desirable to provide a plurality of operation instructions stepwise in a predetermined sequence. For example, the following instructions may be output stepwise: an instruction to perform a translational movement in a direction orthogonal to the electronic scan direction (i.e., in the forward/rearward direction), an instruction to perform a translational movement in a direction along the electronic scan direction (i.e., in the rightward/leftward direction), an instruction to perform a rotational movement about the central axis of the probe, a tilting instruction to tilt the probe such that a line normal to the scan plane becomes tilted, a tilting instruction to tilt the probe while maintaining the orientation of a line normal to the scan plane, and the like. This sequence of instructions may be repeated.

A table 46 shown in FIG. 2 illustrates example management of tissue models and observation cross sections. In FIG. 2, the field denoted by reference numeral 28A corresponds to the tissue model group storage unit described above, and the fields denoted by reference numeral 40A correspond to the target cross section management table described above. In the table 46, the fields of target tissue 48, examinee body position 50, type of approach 52, tissue model 54, observation cross section 56, and target cross section position 58 are provided along the horizontal direction.

As the target tissue 48, a plurality of tissues which can possibly be an examination target are registered. As the examinee body position 50, a plurality of body positions (supine, lateral recumbent, and the like) are registered. The type of approach 52 serves to identify the location and orientation of the probe when abutted. Regarding the heart, known types of approach include: a type in which the probe is abutted against the chest surface and ultrasound is transmitted/received through the intercostal spaces; a type in which the probe is abutted obliquely against the upper abdomen and ultrasound transmission/reception is performed with respect to the apex of the heart; and the like. As the tissue model 54, one or more tissue models are provided for each of the tissues. As the observation cross section 56, a plurality of observation cross sections to be sequentially selected according to an examination protocol are registered. Each observation cross section regarding which navigation is to be provided may be selected by the user. As the target cross section position 58, positions of target cross sections corresponding to the respective observation cross sections are managed. Each of the positions is, for example, a position in a tissue model coordinate system.

Figure 3:
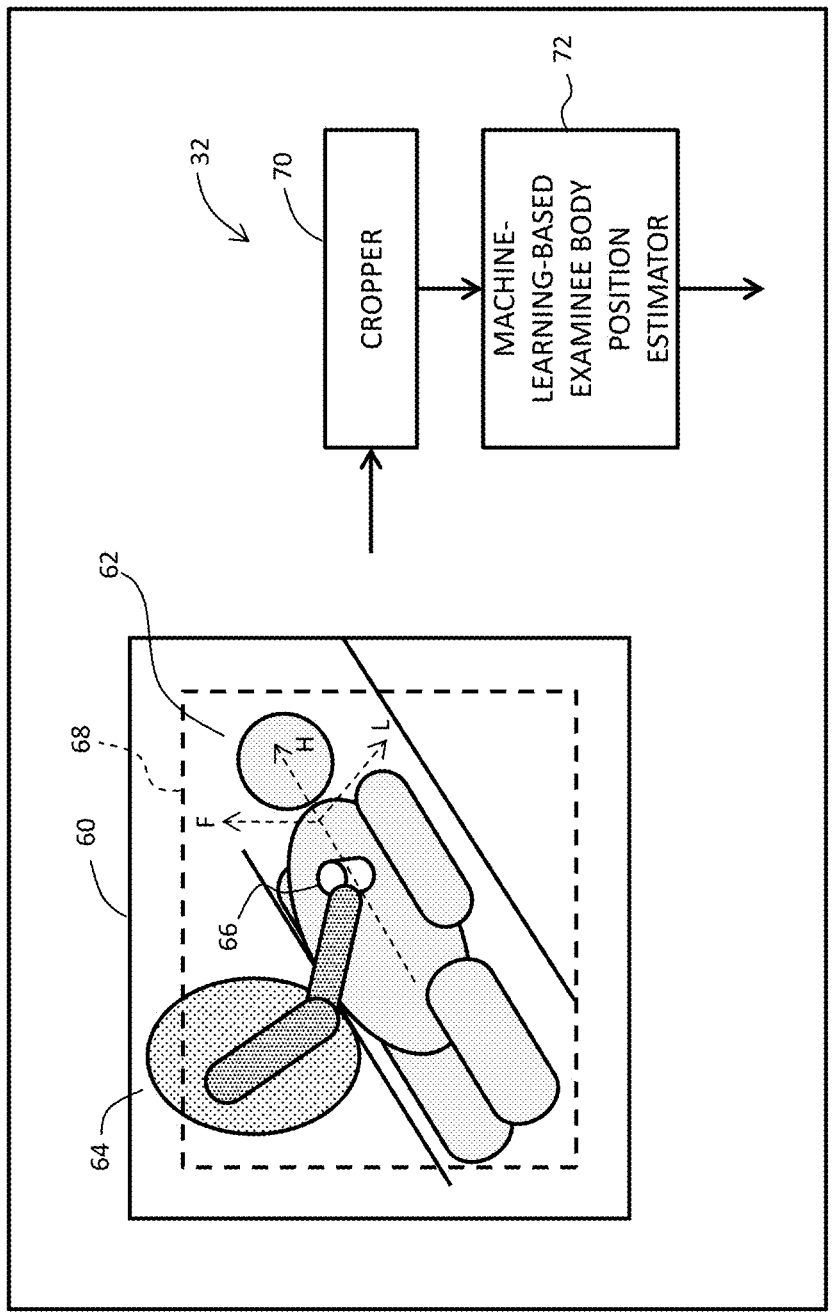
FIG. 3 is a diagram for explaining a method of estimating an examinee's body position.

FIG. 3 schematically illustrates a method of determining an examinee's body position. In the example shown, a camera image 60 includes an examinee image 62, an examiner image 64, a probe image 66, and so on. The examinee body position determining unit 32 includes a cropper (extractor) 70 and a machine-learning-based examinee body position estimator 72. By means of the cropper 70, an image portion 68 to be supplied to the examinee body position estimator 72 is cropped out of the camera image 60. For example, the image portion 68 may be determined on the basis of the examinee image 62.

The examinee body position estimator 72 is constituted of, for example, a CNN (convolutional neural network). The examinee body position estimator 72 can be configured by supplying a large amount of training data to the CNN in advance thereby causing the CNN to perform learning. When the image portion 68 is input into the examinee body position estimator 72, a specific body position such as, for example, a supine position with the face upward is estimated. As a result of the body position estimation, the examinee coordinate system is determined. For example, the head direction H, the left direction L, and the front direction F are determined.

Figure 4:
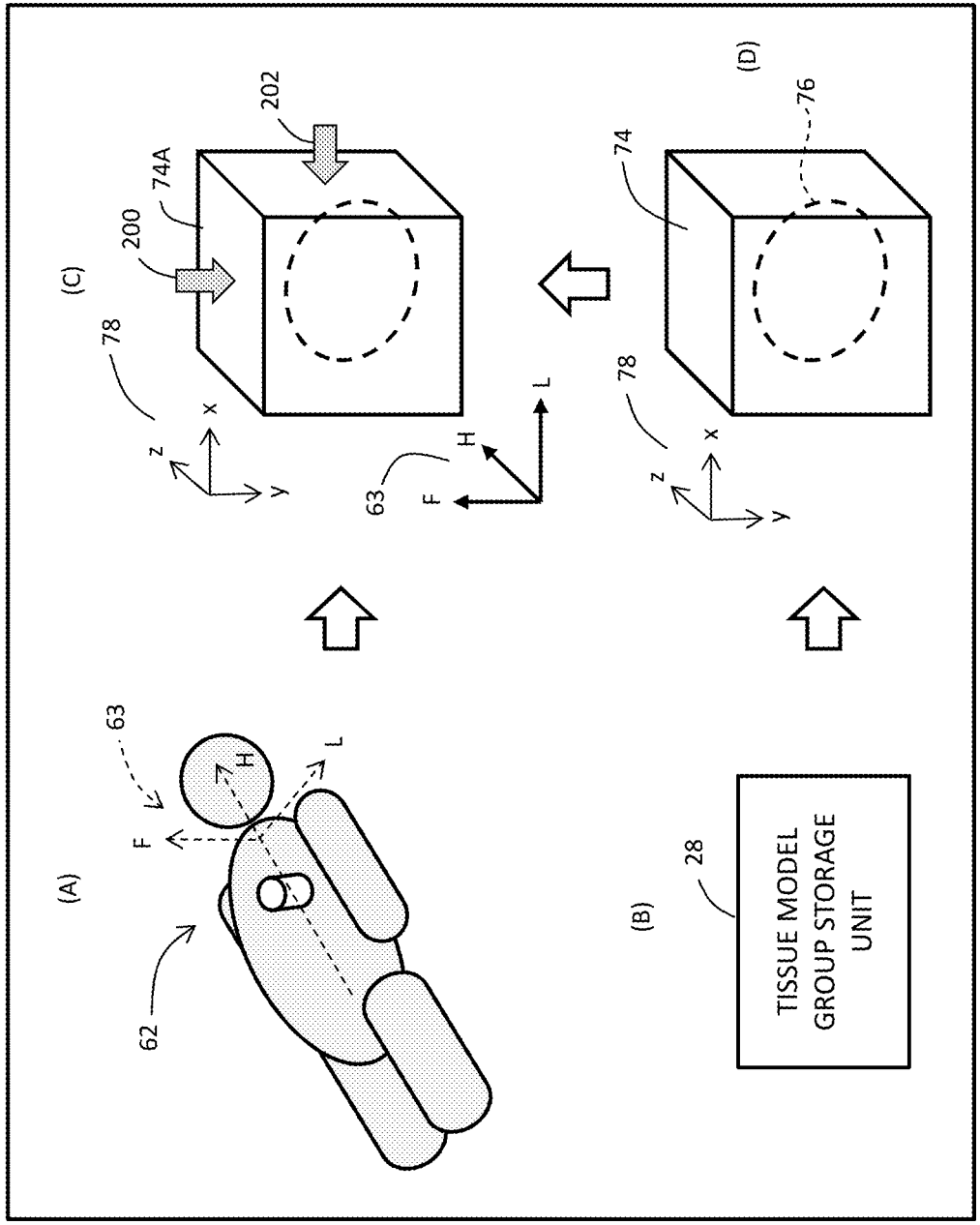
FIG. 4 is a diagram for explaining a method of aligning coordinate systems.

FIG. 4 schematically illustrates a coordinate system aligning method. As shown at (A), in an examinee image 62, an examinee coordinate system 63 can be conceived as described above. Meanwhile, as shown at (B) and (C), a tissue model 74 corresponding to the target tissue is selected from the tissue model group storage unit 28. The tissue model 74 has a tissue model coordinate system 78. In the example shown, the tissue model coordinate system 78 has an x-direction, a y-direction, and a z-direction. Reference numeral 76 denotes a structure (e.g., the four chambers of the heart) within the tissue model 74.

As shown at (C), the above-described coordinate system aligning unit 34 executes a processing of aligning the examinee coordinate system 63 and the tissue model coordinate system 78. For example, by rotating the tissue model coordinate system 78, the tissue model coordinate system 78 is caused to conform to the examinee coordinate system 63. Reference numeral 74A denotes the tissue model after the coordinate system alignment. In the example shown, the x-direction is correlated to the L direction, the −y-direction is correlated to the F direction, and the z-direction is correlated to the H direction. Here, it is sufficient to perform the alignment of the coordinate systems according to required accuracy. In cases where the scan plane is eventually caused to coincide with an observation cross section by visual determination by the examiner, the alignment of the coordinate systems may be performed roughly. Based on the examinee's body position, a tissue model conforming thereto (i.e., requiring no rotation or the like) may be selected. In that case, the coordinate system alignment is unnecessary.

After the coordinate system alignment, a range of area in which the originating point of ultrasound transmission/reception can be set (corresponding to a range of probe abutment area) can be limited based on relationship with the tissue model 74A. For example, two faces or portions denoted by reference numerals 200 and 202 are regions in which the originating point of ultrasound transmission/reception can be set. In cases where the type of approach can be determined, it is possible to further narrow down the range of area in which the originating point of ultrasound transmission/reception is to be set. By narrowing down the range of area in which the originating point of ultrasound transmission/reception can be set, the number of provisional cross sections that should be set with respect to the tissue model can be reduced.

Figure 5:
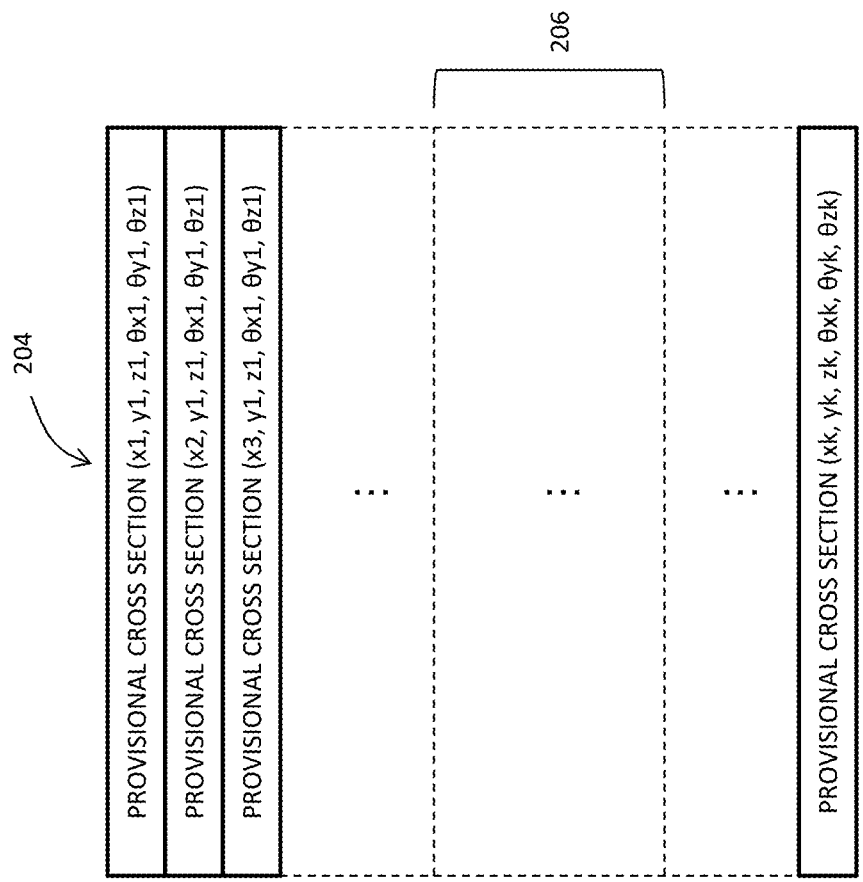
FIG. 5 is a diagram for explaining selection of a group of provisional cross sections.

FIG. 5 shows a provisional cross section list 204 including all provisional cross sections that can theoretically be set with respect to a tissue model. In accordance with a range of area in which the originating point of ultrasound transmission/reception can be set, a range 206 of provisional cross sections to be actually set with respect to the tissue model can be narrowed down. As a result, the amount of calculation to be performed at the time of determining the position of the current cross section can be greatly reduced.

Figure 6:
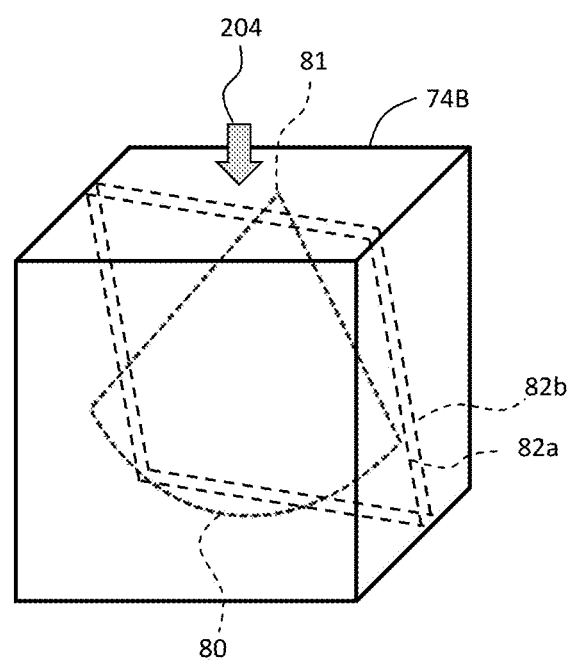
FIG. 6 is a diagram showing example provisional cross sections set in a tissue model.

FIG. 6 shows provisional cross sections 82*a*, 82*b*, which are a part of the provisional cross sections set in a tissue model 74B after coordinate system alignment. Reference numeral 80 denotes a region corresponding to the scan plane, and reference numeral 81 denotes a position corresponding to the originating point of ultrasound transmission/reception. A degree of similarity is calculated between data of the provisional cross section 82a and the tomographic image data, and subsequently, a degree of similarity is calculated between data of the provisional cross section 82b and the tomographic image data. Such processing is repeated, and the provisional cross section that results in the best similarity is identified as the current cross section corresponding to the scan plane. Specifically, the provisional cross section that includes the region 80 is identified as the current cross section. In that case, for example, the face or portion denoted by reference numeral 204 is determined as the range of area in which the originating point of ultrasound transmission/reception can be set.

Figure 7:
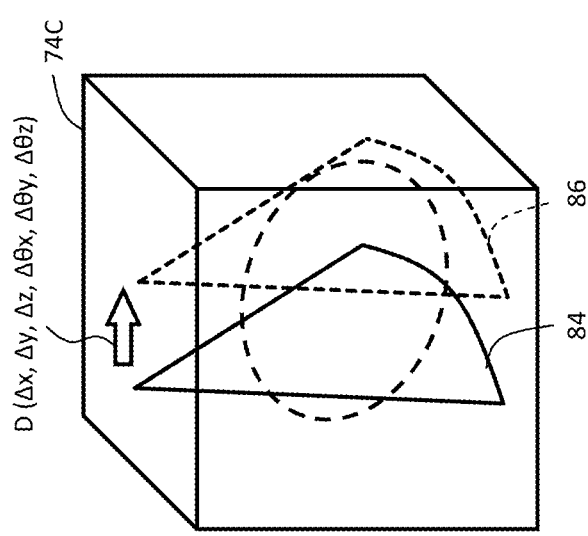
FIG. 7 is a diagram showing a current cross section and a target cross section which are located away from each other.

FIG. 7 shows a spatial relationship between a current cross section 84 and a target cross section 86 within a tissue model 74C. Difference information D is generated between the current cross section 84 and the target cross section 86, and based on this difference information D, operation support information is generated.

Figure 8:
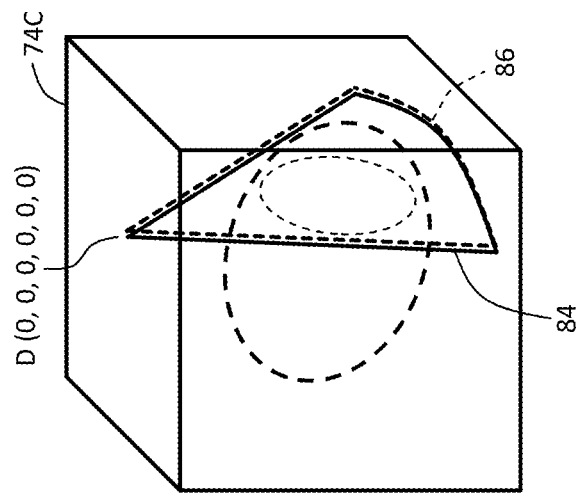
FIG. 8 is a diagram showing a current cross section and a target cross section which coincide with each other.

FIG. 8 shows another spatial relationship between the current cross section 84 and the target cross section 86 within the tissue model 74C. The current cross section 84 and the target cross section 86 substantially coincide with each other. The difference information D indicates this coincidence.

Figure 9:
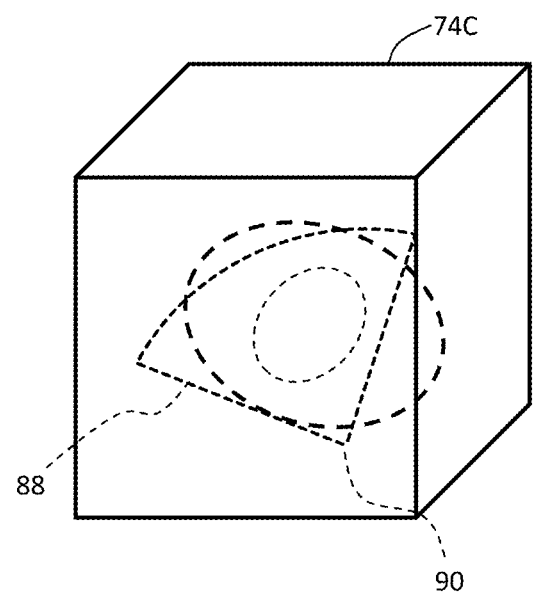
FIG. 9 is a diagram showing another current cross section.

FIG. 9 shows another region 88 corresponding to a scan plane within the tissue model 74C. Reference numeral 90 denotes a position corresponding to the originating point of ultrasound transmission/reception. A provisional cross section that includes the region 88 is to be identified as the current cross section as a result of a matching processing.

Figure 10:
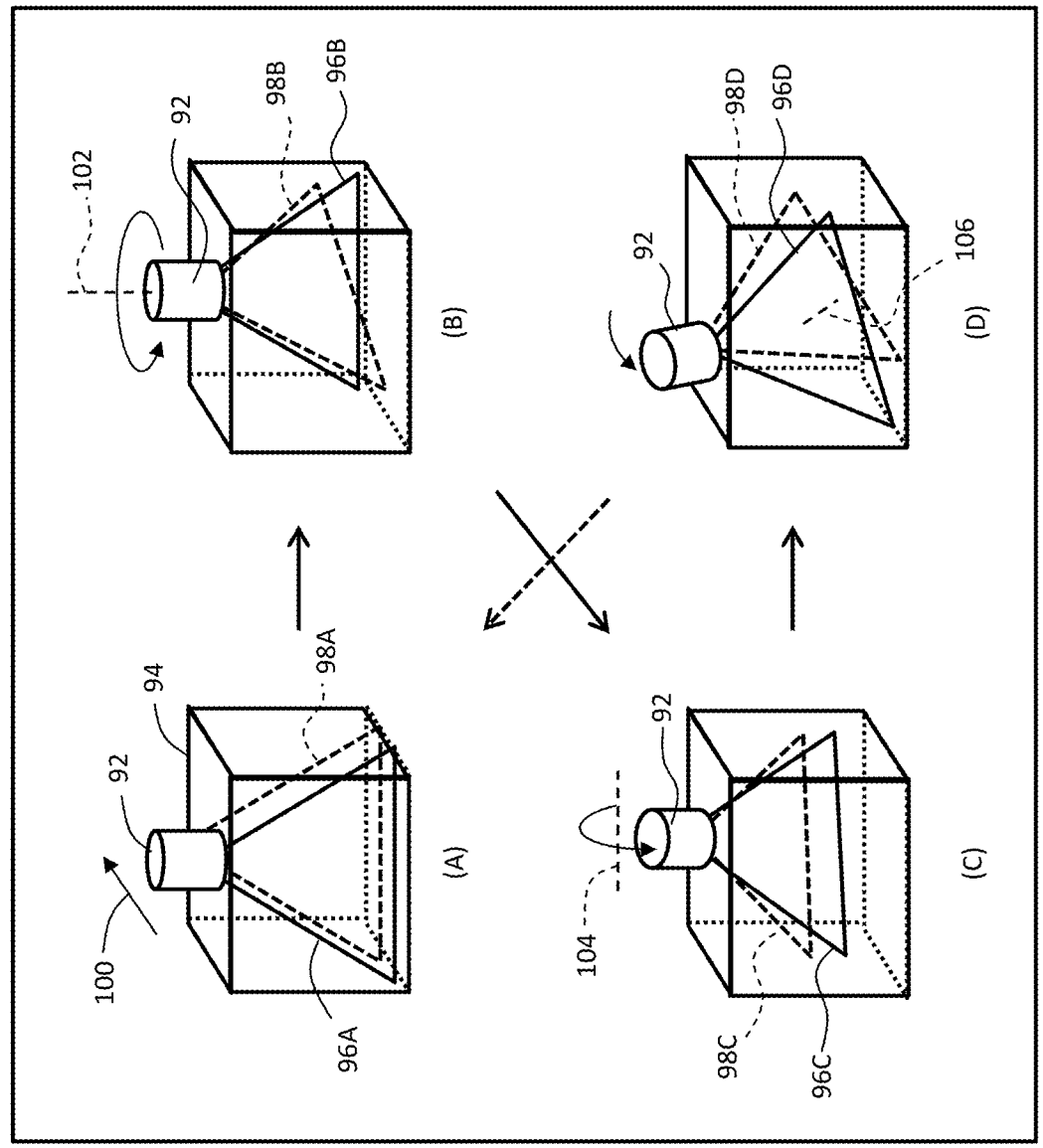
FIG. 10 is a diagram illustrating a procedure at the time of navigation.

FIG. 10 schematically illustrates an operation support process. In the operation support process, as shown at (A)~(D), a plurality of operation instructions are provided stepwise to the examiner. In the example shown, first, as shown at (A), an instruction to perform a movement in the forward/rearward direction of the probe 92 (i.e., a movement in a direction orthogonal to the scan plane) is provided (see reference numeral 100). Before or after that, an instruction to perform a movement in the rightward/leftward direction of the probe 92 (i.e., a movement in a direction along the electronic scan direction) may also be provided. Reference numeral 94 denotes a three-dimensional space in the examinee's body. Reference numeral 96A denotes a scan plane before the movement, while reference numeral 98A denotes a scan plane after the movement.

Next, as shown at (B), an instruction to perform a rotational movement of the probe 92 (i.e., a movement about the probe central axis 102) is provided. Reference numeral 96B denotes a scan plane before the movement, while reference numeral 98B denotes a scan plane after the movement. Subsequently, as shown at (C), an instruction to perform a first tilting movement of the probe 92 (i.e., a movement about a horizontal axis 104 parallel to the scan plane) is provided. Reference numeral 96C denotes a scan plane before the movement, while reference numeral 98C denotes a scan plane after the movement. Finally, as shown at (D), an instruction to perform a second tilting movement of the probe 92 (i.e., a movement which causes a line 106 normal to a scan plane to be translated, and which is performed with the originating point of ultrasound transmission/reception serving as the center of rotation) is provided. Reference numeral 96D denotes a scan plane before the movement, while reference numeral 98D denotes a scan plane after the movement. When the current cross section does not coincide with or does not closely approach the target cross section even after the above-described operation support process is performed, the respective steps may be executed repeatedly.

Figure 11:
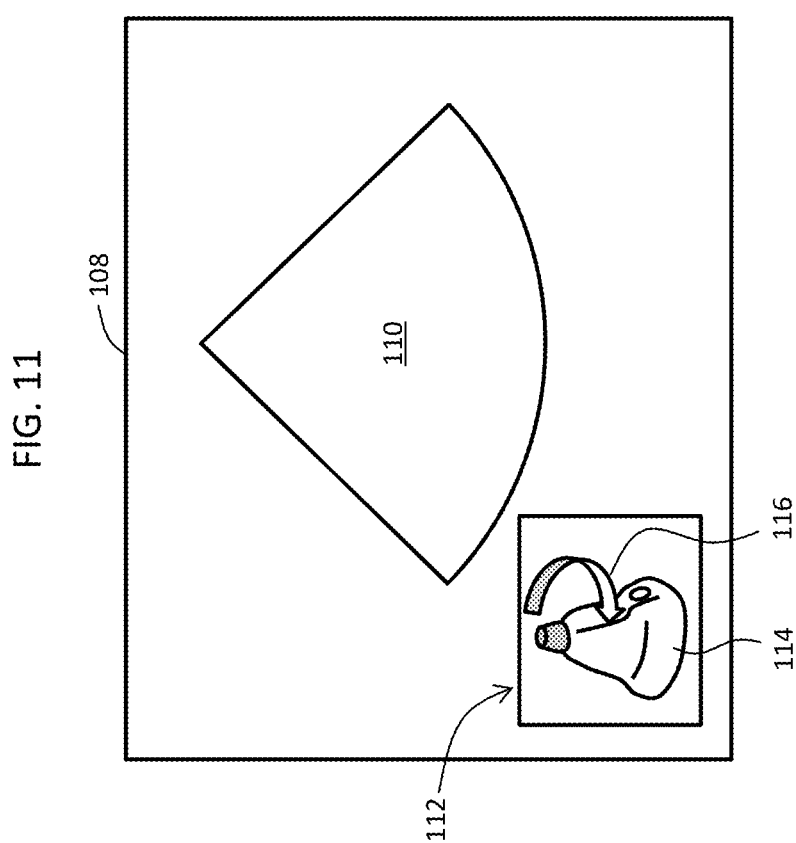
FIG. 11 is a diagram showing an example navigation image.

FIG. 11 shows an example operation guide image. On a screen 108 of a display, an operation guide image 112 is displayed together with an ultrasound image 110. The operation guide image 112 is composed of a probe image 114 and an instruction mark 116. A plurality of instruction marks corresponding to a plurality of instruction types are provided and selectively used. At the time of displaying an operation guide image, a model simulating the examinee's body may be displayed. Together with the operation guide image, an instruction of a movement direction (for example, a direction approaching the head, or a direction approaching the left arm) with respect to the examinee may be provided in text or vocally.

Figure 12:
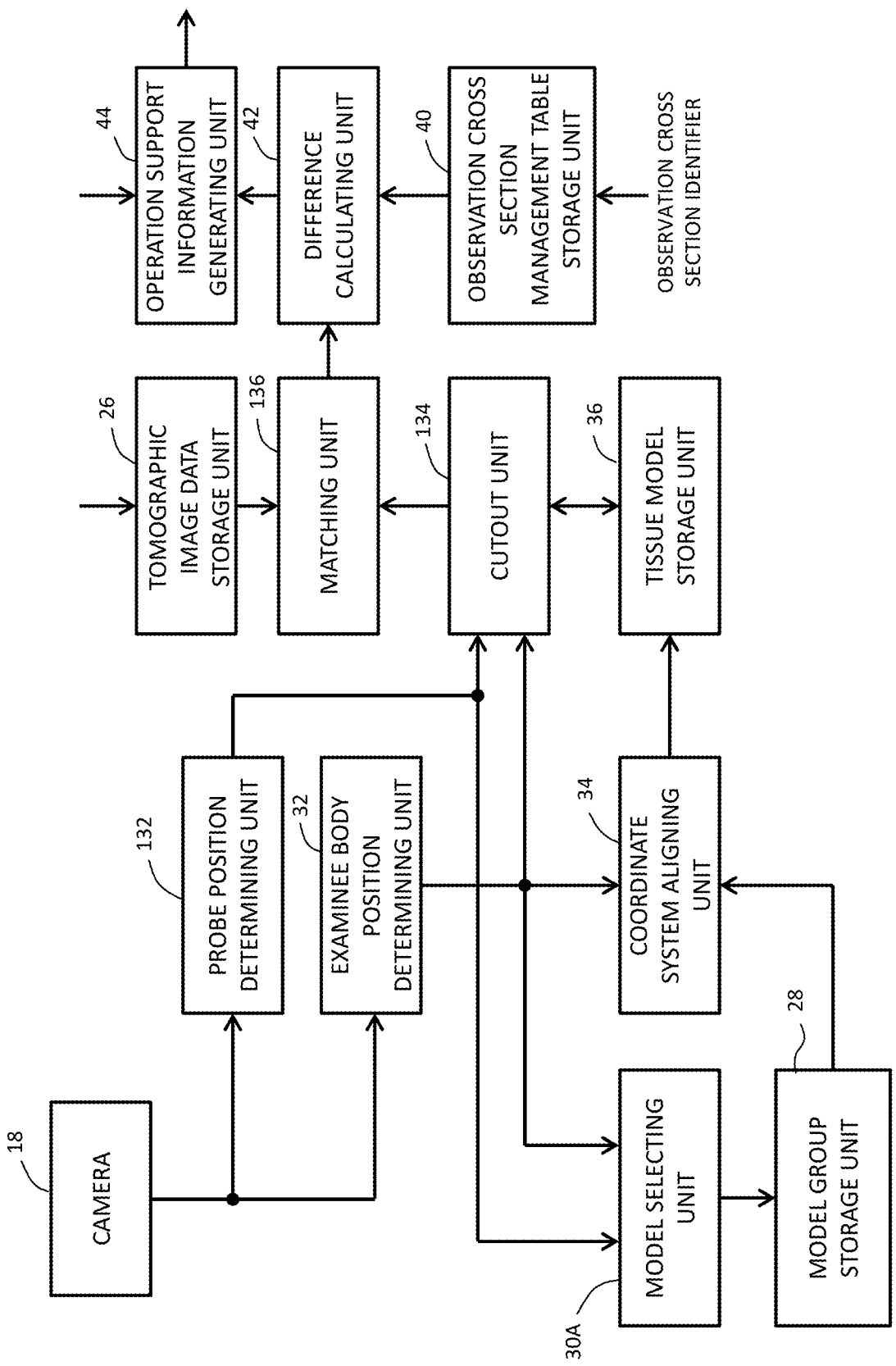
FIG. 12 is a block diagram illustrating a first modified embodiment.

FIG. 12 shows an essential part of a configuration according to a modified embodiment. In FIG. 12, elements identical to those shown in FIG. 1 are labeled with the same reference numerals, and description thereof will not be repeated.

In the modified embodiment shown in FIG. 12, a probe position determining unit 132 is provided. The probe position determining unit 132 is a second determiner which determines, based on a camera image, the probe position relative to the examinee. A probe position is determined as being, for example, in front or on a side of the chest of the examinee in a supine position. Based on this, it is possible to automatically determine the type of approach, or determine a spatial relationship between the tissue model and the probe, or identify the target tissue. As a result, a range of area in which the current cross section can occur can be narrowed down, or the target tissue can be automatically identified.

From the probe position determining unit 132, information indicating the probe position is supplied to a cutout unit 134 and a model selecting unit 30A. The model selecting unit 30A automatically determines the target tissue based on the examinee's body position and the probe position, and based on the determined target tissue, selects a specific tissue model to be used.

In the embodiment shown, the current cross section searching unit is composed of the cutout unit 134 and a matching unit 136. The cutout unit 134 is a unit that sequentially cuts out a plurality of sets of provisional cross section data from the tissue model. When doing so, the cutout unit 134 adaptively or restrictively determines the range of provisional cross sections based on the examinee's body position and the probe position. In other words, a group of provisional cross sections is narrowed down based on the examinee's body position and the probe position. The matching unit 136 executes a correlation calculation between each of the sets of provisional cross section data and the tomographic image data, thereby computing a degree of similarity for each set of provisional cross section data. Based on this, the current cross section is determined.

Figure 13:
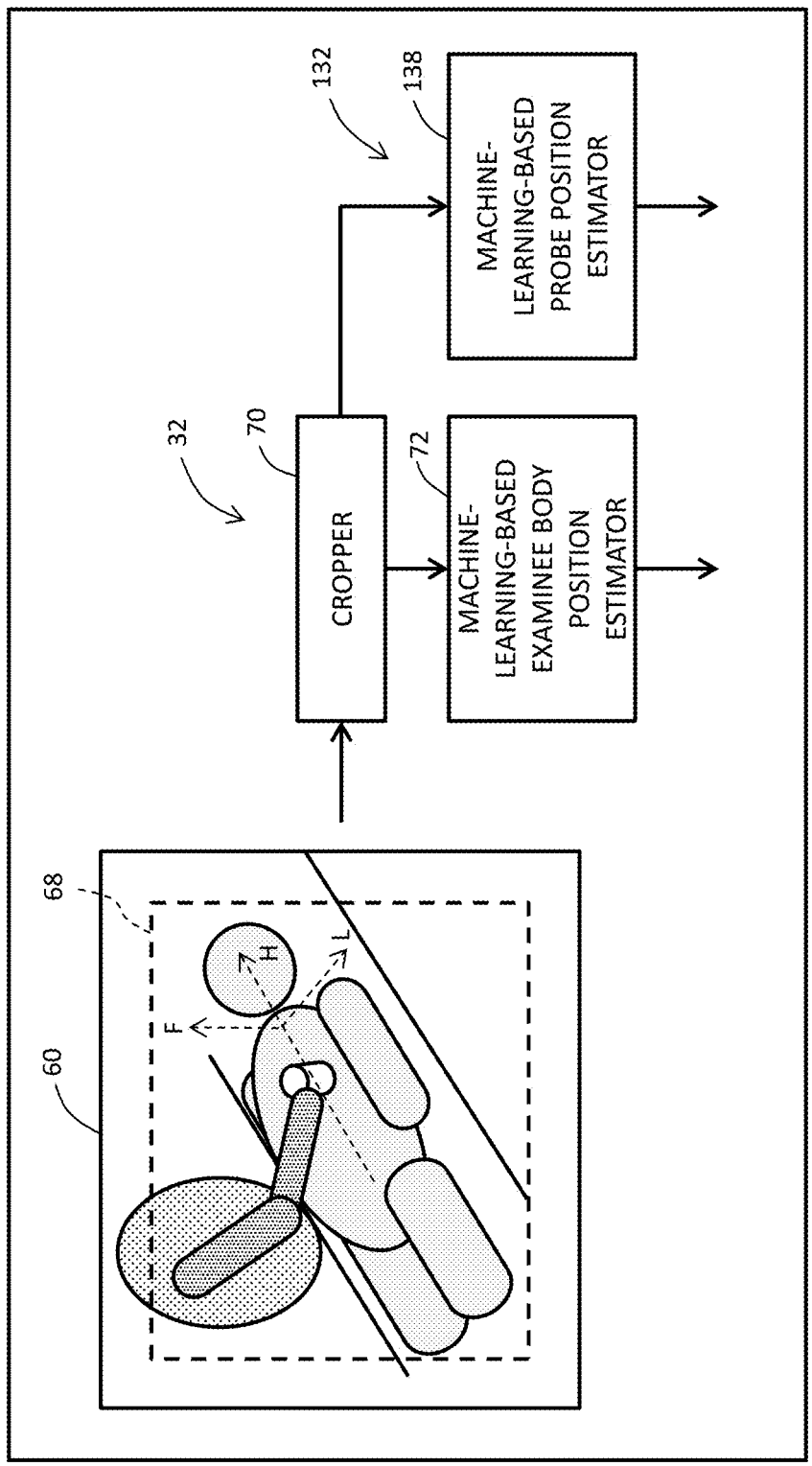
FIG. 13 is a diagram for explaining a camera image processing performed in the first modified embodiment.

FIG. 13 shows an example configuration of the examinee body position determining unit 32 and the probe position determining unit 132 according to a modified embodiment. An image portion 68 is cropped out of a camera image 60 by the cropper 70. The machine-learning-based examinee body position estimator 72 estimates the examinee's body position based on the image portion 68. The probe position determining unit 132 is composed of a machine-learning-based probe position estimator 138, which is constituted of a learned CNN. The machine-learning-based probe position estimator 138 estimates the probe position based on the image portion 68. When doing so, the probe orientation may also be estimated. A single estimator may be used to simultaneously estimate both of the examinee's body position and the probe position.

According to the above-described embodiments, the position of the scan plane relative to an observation cross section can be determined in a simple manner without using a positioning system having a complex configuration, and in addition, operation support information can be generated based on the spatial relationship between the positions of the scan plane and the observation cross section. In determining the position of the scan plane; i.e., the position of the current cross section, since a group of provisional cross sections to be used in the matching calculation can be narrowed down by camera image analysis, the amount of calculation can be reduced, and calculation accuracy can be enhanced.

The invention claimed is:

1. An ultrasonic diagnosis system, comprising:
a former configured to form a tomographic image based on information obtained from a scan plane created by a probe;
a memory having a tissue model stored therein, wherein the tissue model reflects a three-dimensional structure of a target tissue;
a camera configured to capture an examinee image of an examinee against which the probe is abutted, thereby obtaining a camera image including the examinee image;
a determiner configured to determine a body position of the examinee based on the examinee image;
a searcher configured to select, based on the body position of the examinee, a group of provisional model cross sections from provisional cross sections which can be set with respect to the tissue model, set the group of provisional model cross sections with respect to the tissue model, and identify a current model cross section corresponding to the scan plane by comparing the tomographic image to the group of provisional model cross sections, the current model cross section being one of the provisional cross sections; and
a generator configured to generate, based on the current model cross section, probe operation support information for causing the scan plane to approach an observation cross section in the target tissue, wherein the probe operation support information is information for a probe movement and the observation cross section is a cross section which should be diagnosed in the target tissue, and
wherein the tomographic image and the probe operation support information are displayed simultaneously.

2. The ultrasonic diagnosis system according to claim 1, wherein
the memory has a plurality of tissue models stored therein, wherein as said tissue model, a specific tissue model corresponding to the target tissue is selected from among the plurality of tissue models, and
the group of provisional model cross sections is set with respect to the specific tissue model.

3. The ultrasonic diagnosis system according to claim 1, wherein
a target model cross section corresponding to the observation cross section is determined in the tissue model, and
the generator is further configured to generate the probe operation support information based on a spatial relationship between the current model cross section and the target model cross section in the tissue model.

4. The ultrasonic diagnosis system according to claim 1, wherein
the camera image includes a probe image,
the determiner is further configured to determine a position of the probe based on the probe image, and
based on the position of the probe, the searcher is further configured to set the group of provisional model cross sections with respect to the tissue model.

5. The ultrasonic diagnosis system according to claim 2, further comprising:
a selector configured to select, based on the camera image including the examinee image and a probe image, the specific tissue model corresponding to the target tissue from among the plurality of tissue models.

6. The ultrasonic diagnosis system according to claim 1, wherein
the generator is further configured to generate, as the probe operation support information, a plurality of sets of probe movement instruction information sequentially.

7. The ultrasonic diagnosis system according to claim 1, wherein the tissue model is a set of volume data obtained by ultrasound transmission and reception.

8. An operation support method, comprising the steps of:
storing a tissue model which reflects a three-dimensional structure of a target tissue;
capturing, with a camera, a camera image including an examinee image of an examinee;
determining a body position of the examinee based on the examinee image;
selecting, based on the body position of the examinee, a group of provisional model cross sections from provisional cross sections set with respect to a tissue model, set the group of provisional model cross sections with respect to the tissue model, and comparing a tomographic image, which is formed based on information obtained from a scan plane created by a probe, to the group of provisional model cross sections, thereby identifying a current model cross section corresponding to the scan plane;
generating probe operation support information based on a spatial relationship between the current model cross section and a target model cross section in the tissue model, the probe operation support information being information for a probe movement; and
displaying the tomographic image and the probe operation support information simultaneously.

9. A non-transitory storage medium having stored therein a program for executing an operation support method in an ultrasonic diagnosis system, the operation support method comprising:
storing a tissue model which reflects a three-dimensional structure of a target tissue;
capturing, with a camera, a camera image including an examinee image of an examinee;
determining a body position of the examinee based on the examinee image;
selecting, based on the body position of the examinee, a group of provisional model cross sections from provisional cross sections set with respect to a tissue model, set the group of provisional model cross sections with respect to the tissue model, and comparing a tomographic image, which is formed based on information obtained from a scan plane created by a probe, to the group of provisional model cross sections, thereby identifying a current model cross section corresponding to the scan plane;

generating probe operation support information based on a spatial relationship between the current model cross section and a target model cross section in the tissue model, the probe operation support information being information for a probe movement; and
displaying the tomographic image and the probe operation support information simultaneously.

\* \* \* \* \*